(12) United States Patent
Wu et al.

(10) Patent No.: US 9,161,703 B2
(45) Date of Patent: Oct. 20, 2015

(54) INTEGRATED BIOINFORMATICS SENSING APPARATUS

(71) Applicants: Min-Hsien Wu, Kaohsiung (TW); Yi-Yuan Chiu, New Taipei (TW); Hsin-Yao Wang, Chiayi (TW); Song-Bin Huang, New Taipei (TW)

(72) Inventors: Min-Hsien Wu, Kaohsiung (TW); Yi-Yuan Chiu, New Taipei (TW); Hsin-Yao Wang, Chiayi (TW); Song-Bin Huang, New Taipei (TW)

(73) Assignee: CHANG GUNG UNIVERSITY, Taoyuan County (TW)

( * ) Notice: Subject to any disclaimer, the term of this patent is extended or adjusted under 35 U.S.C. 154(b) by 150 days.

(21) Appl. No.: 14/053,639

(22) Filed: Oct. 15, 2013

(65) Prior Publication Data
US 2014/0107452 A1 Apr. 17, 2014

(30) Foreign Application Priority Data
Oct. 16, 2012 (TW) .............................. 101138048 A

(51) Int. Cl.
| A61B 5/04 | (2006.01) |
| A61B 5/024 | (2006.01) |
| A61B 5/11 | (2006.01) |
| A61B 5/113 | (2006.01) |
| A61B 5/00 | (2006.01) |

(52) U.S. Cl.
CPC .............. *A61B 5/04* (2013.01); *A61B 5/02438* (2013.01); *A61B 5/02444* (2013.01); *A61B 5/113* (2013.01); *A61B 5/1107* (2013.01); *A61B 5/6813* (2013.01); *A61B 2560/0412* (2013.01); *A61B 2560/0468* (2013.01); *A61B 2562/0209* (2013.01); *A61B 2562/182* (2013.01)

(58) Field of Classification Search
CPC .......................... A61B 2562/0209; A61B 5/04
USPC .......... 600/372, 382, 384, 386, 391, 392, 595
See application file for complete search history.

(56) References Cited

U.S. PATENT DOCUMENTS

| 4,509,527 | A | * | 4/1985 | Fraden | 600/484 |
| 4,763,660 | A | * | 8/1988 | Kroll et al. | 600/391 |
| 4,947,859 | A | * | 8/1990 | Brewer et al. | 600/528 |
| 5,365,937 | A | * | 11/1994 | Reeves et al. | 600/528 |
| 5,448,996 | A | * | 9/1995 | Bellin et al. | 600/574 |
| 5,467,768 | A | * | 11/1995 | Suda et al. | 600/391 |
| 5,807,268 | A | * | 9/1998 | Reeves et al. | 600/528 |
| 5,913,829 | A | * | 6/1999 | Reeves et al. | 600/528 |
| 6,297,738 | B1 | * | 10/2001 | Newham | 340/573.1 |
| 2003/0036691 | A1 | * | 2/2003 | Stanaland et al. | 600/372 |
| 2007/0049837 | A1 | * | 3/2007 | Shertukde | A61B 5/0408 600/528 |

* cited by examiner

*Primary Examiner* — Lee S Cohen

(57) ABSTRACT

An integrated bioinformatics sensing apparatus includes a piezoelectric sensing layer, an upper conductive layer, a bottom conductive layer and an information transmission controller. The piezoelectric sensing layer senses a physiological rhythm of a living organism to output a physiological rhythm signal, and the upper and bottom conductive layers sense a physiological electrical signal on a body surface of the living organism. The information transmission controller receives and processes the physiological rhythm signal and the physiological electrical signal to generate and store the sensed bioinformatics, or transmit the signals to the external processing device to display the sensed bioinformatics. The simple-structured sensing apparatus can be attached onto the body surface of the living organism conveniently.

12 Claims, 1 Drawing Sheet

INTEGRATED BIOINFORMATICS SENSING APPARATUS

FIELD OF THE INVENTION

The present invention relates to an integrated bioinformatics sensing apparatus and, in particular, to the bioinformatics sensing apparatus with two conductive layers attached or coated onto upper and bottom surfaces of a piezoelectric sensing layer, with the two conductive layers and the piezoelectric sensing layer provided for sensing a physiological electrical signal and a physiological rhythm signal of a living organism respectively.

BACKGROUND OF THE INVENTION

In a living organism, a feeble electric signal is generated by signals transmitted by nerves of the living organism due to a change of ion concentration. Thus, an appropriate sensing apparatus can be installed at a specific position to sense the operation of a specific organ indirectly. For instance, several electrodes are attached onto the skin of a user's chest and at positions near the user's heart, so that the current or voltage sensed by the electrodes can be processed by a signal processing device to generate a signal, such as an electrocardiogram signal, that represents a physiological status of the user's heart.

In addition, body movements of a living organism achieved by stretching and contracting muscles may cause a skin deformation, and the skin may produce regular tension and soothe in the up-and-down chest or abdominal movements during breathing. Therefore, a piezoelectric element can be used to convert the skin deformation into a corresponding physiological rhythm signal, to achieve the effect of sensing the body movement, heartbeat or breathing movement of the living organism.

However, the drawback of the aforementioned prior art resides on the requirement of using the electrocardiogram electrodes to sense the electrocardiogram and the piezoelectric elements to sense the physiological rhythm, thus causing tremendous inconvenience to users. In particular, conductive wires are connected to the electrocardiogram electrodes and piezoelectric elements for transmitting the generated electrical signal to an external processing device and displaying the information of the electrocardiogram and physiological rhythm. The sensing devices and conductive wires are attached all over an examinee's body, and thus will lead to visual confusions in clinical practice. In the meantime, the sensing devices and conductive wires may be pulled and separated from the sensing apparatuses, and thus will result in a failure of an examination.

SUMMARY OF THE INVENTION

Therefore, it is a primary objective of the present invention to overcome the aforementioned problem of the prior art by providing an integrated bioinformatics sensing apparatus installed on a body surface of a living organism to sense bioinformatics of the living organism. The bioinformatics sensing apparatus comprises: a piezoelectric sensing layer, an upper conductive layer, a bottom conductive layer and an information transmission controller. The piezoelectric sensing layer senses a physiological rhythm of the living organism to generate a corresponding physiological rhythm signal, and the upper and/or bottom conductive layers sense a physiological electrical signal on a body surface of the living organism to generate a physiological sensing electrical signal. The bottom conductive layer and the upper conductive layer are provided for sensing a physiological electrical signal coming from a body surface of the living organism to generate and output a physiological sensing electrical signal, and the information transmission controller receives and processes the physiological rhythm signal and the physiological sensing electrical signal to generate and store the sensed bioinformatics, and/or transmit the sensed bioinformatics to an external processing device for the display of the sensed bioinformatics.

The piezoelectric sensing layer can be a flat or curved film, sheet, wire or cable capable of converting a mechanical deformation of the piezoelectric sensing layer into an electrical signal to be outputted. The upper and bottom conductive layers can be coated or attached onto a part or the whole of the upper surface and a part or the whole of the bottom surface of the piezoelectric sensing layer respectively for sandwiching the piezoelectric sensing layer therebetween. The bottom conductive layer can be contacted directly, with the body surface of the living organism, so that the bottom conductive layer can sense the physiological electrical signal at the body surface of the living organism while the piezoelectric sensing layer can sense a physiological rhythm of the living organism. the physiological rhythm of the living organism includes a breathing rhythm, a heartbeat pulse, a body movement, or a muscle contraction, and the physiological electrical signal includes an electrocardiogram, an electroencephalogram, an electromyogram, an electroneurogram, an electroretinogram, an electrogastrography, an electroneuromyography, an electrocorticogram, an electrooculography and an electronysagmography, depending on the installation position of the sensing apparatus.

Therefore, the present invention provides the function of sensing both a physiological electrical signal and a physiological rhythm of a living organism at the same time and has the features of simple structure and convenient use.

DESCRIPTION OF THE PREFERRED EMBODIMENTS

Figure 1:
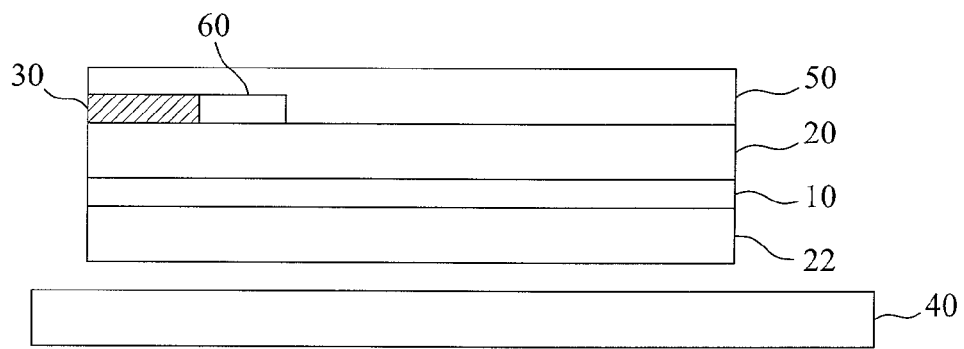
FIG. 1 is a schematic view of an integrated bioinformatics sensing apparatus of a preferred embodiment of the present invention.

With reference to FIG. 1 for an integrated bioinformatics sensing apparatus of the present invention, the integrated bioinformatics sensing apparatus comprises a piezoelectric sensing layer 10, an upper conductive layer 20 and a bottom conductive layer 22. The integrated bioinformatics sensing apparatus is attached onto a body surface 40 of the living organism for sensing bioinformatics of the living organism including a physiological electrical signal and a physiological rhythm signal of the living organism. In particular, the bottom conductive layer 22 is in contact with the body surface 40 to generate and output the sensed bioinformatics. The body surface 40 can be human chest skin, abdominal skin, head skin, neck skin, limb joint skin or facial skin, and it also can be a skin surface of any living organism.

The piezoelectric sensing layer 10 is a flat or curved film, sheet, wire or cable having an upper surface and a bottom surface. The piezoelectric sensing layer 10 is made of electromechanical film, polyamide, $PbTiO_3$, quartz, $SiO_2$, LiNbO$_3$, LiTaO$_3$, BaTiO$_3$, Pb(Zr,Ti)O$_3$, GaAs, AlN, ZnO, BiFeO$_3$, polyvinylidene fluoride, polyethylene terephthalate, polyethylene, polypropylene, polyvinyl chloride, polystyrene, polytetrafluoroethene, polymethyl methacrylate and polydimethyl siloxane.

The piezoelectric sensing layer 10 has a piezoelectric conversion function for sensing a physiological rhythm at a body surface 40 of the living organism to generate a corresponding physiological rhythm signal. For instance, the chest or abdominal skin may produce a deformation caused by stretching and contracting the skin continuously when breathing, and the piezoelectric sensing layer 10 can sense the deformation to generate an electrical signal corresponding to the physiological rhythm of the breathing movement (that is the physiological rhythm signal.) In addition, the piezoelectric sensing layer 10 senses the deformation of limb joint skin caused by walking, to generate a physiological rhythm signal corresponding to the walking movement. Therefore, the physiological movements including a facial expression and movement, a hand swing or grip, a neck rotation and a waist bending drive the body surface 40 to generate a corresponding physiological rhythm, and the piezoelectric sensing layer 10 senses and generates a corresponding physiological rhythm signal.

The upper conductive layer 20 and/or bottom conductive layer 22 are made of a conductive material such as a conductive metal, a conductive adhesive, a conductive silver paste, a conductive hydrogel, a conductive foam, a conductive rubber, a conductive polymer, a conductive plastic or a conductive ceramic material and disposed or coated on a part or the whole of the upper surface and a part or the whole of the bottom surface of the piezoelectric sensing layer 10. In other words, the upper and bottom surfaces of the piezoelectric sensing layer 10 are covered by a part or the whole of the upper conductive layer 20 and the bottom conductive layer 22 respectively. Therefore, the upper conductive layer 20 and the bottom conductive layer 22 have the effect of sandwiching and fixing the piezoelectric sensing layer 10. The upper conductive layer 20 and the bottom conductive layer 22 conduct the physiological rhythm, signal sensed by the piezoelectric sensing layer 10 which sense physiological rhythm, and the upper and bottom conductive layers 20, 22 output the physiological rhythm signal.

The upper conductive layer 20 and/or the bottom conductive layer 22 sense the physiological electrical signal at the body surface 40 to generate and output a corresponding physiological sensing electrical signal, and the upper conductive layer 20 and the bottom conductive layer 22 each sense the physiological electrical signal at the body surface 40 to generate and output a corresponding physiological sensing electrical signal. The physiological electrical signal at the body surface 40 is an electrocardiogram, an electroencephalogram, an electromyogram, etc. The physiological electrical signal is primarily caused by the feeble current conducted through the body surface 40. Specifically, the muscle movement of the living organism is controlled by the electrical signal conducted from the brain by the nerve, and the electrical signal of the living organism of this sort is formed by a change of the concentration of ions such as sodium ions or potassium ions, so that some of the electrical signals will be conducted through the body surface 40. Although the electrical signal at the body surface 40 is feeble, an appropriate signal processing can obtain reliable information.

In summation of the description above, a combination of the piezoelectric sensing layer 10 and the upper and bottom conductive layers 20, 22 can sense both a physiological rhythm and a physiological electrical signal and generate and output the physiological rhythm signal and the physiological sensing electrical signal at the same time.

The present invention further comprises an information transmission controller 30 installed onto the upper conductive layer 20 and electrically coupled to the piezoelectric sensing layer 10, the upper conductive layer 20 and/or the bottom conductive layer 22 for receiving a physiological rhythm signal from the piezoelectric sensing layer 10 and a physiological sensing electrical signal from the upper conductive layer 20 and/or the bottom conductive layer 22. The information transmission controller 30 performs a signal processing including amplification, filtering and conversion in order to generate corresponding sensed bioinformatics. In the meantime, the information transmission controller 30 can also store the sensed bioinformatics, such as storing them in an internal memory. The stored bioinformatics are read by an external processing device, and/or the sensed bioinformatics are transmitted to an external processing device via a wireless or cable transmission, and displayed by the external processing device for the user's reference.

Therefore, the external processing device can read the sensed bioinformatics stored by information transmission controller 30 through a remote control method to achieve the remote reading function. In addition, the external processing device further transmits a control instruction to drive the upper conductive layer 20 and/or the bottom conductive layer 22 to generate an electrical signal, to provide an impedance pneumography measurement and/or a functional electrical stimulation, and/or drive the piezoelectric sensing layer 10 to produce a corresponding deformation.

The present invention further comprises a cover layer 50 installed onto the upper conductive layer 20 and covered onto the information transmission controller 30 to provide the protection and isolation effects. The cover layer 50 is made of an electrically insulating material such as polyamide, acrylic, acrylonitrile-butadiene-styrene, phenolic resin, epoxy, polyester, silicone, polyurethane (PU), latex, rubber, glass, food grade silicone, polyethylene terephthalate, polyethylene, polyproylene, polyvinyl chloride, polystyrene, polyvinylidene fluoride, polytetrafluoroethene, polymethyl methacrylate and polydimethyl siloxane.

To reduce external electromagnetic interference, the present invention further comprises an electromagnetic shielding layer made of a conductive electromagnetic shielding material and disposed between the upper conductive layer 20 and the cover layer 50, or disposed on the cover layer 50, or disposed on the bottom conductive layer 22 for providing an electromagnetic shielding function. The electromagnetic shielding material includes a metal, conductive plastic or conductive ceramic material.

Figure 2:
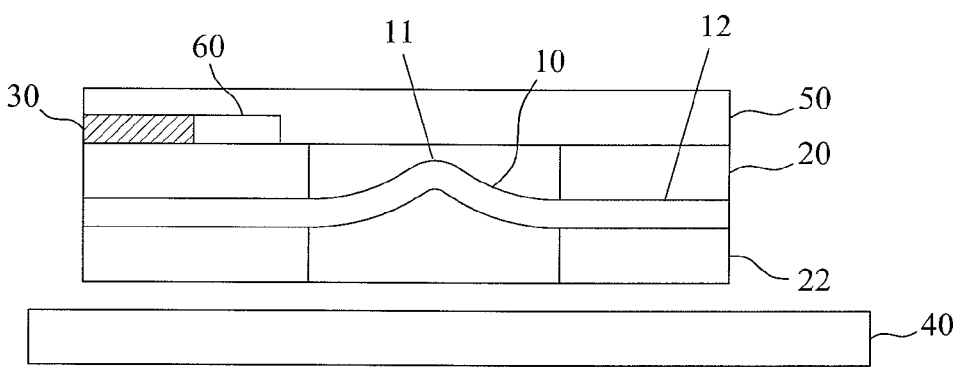
FIG. 2 is a schematic view of an integrated bioinformatics sensing apparatus of another preferred embodiment of the present invention.

With reference to FIG. 2 for another preferred embodiment of the present invention, the piezoelectric sensing layer 10 is a curved film, sheet, wire or cable having at least one curved portion 11 and at least one flat portion 12. In FIG. 2, the integrated bioinformatics sensing apparatus of this preferred embodiment has a plurality of upper conductive layers 20 and a plurality of bottom conductive layers 22 disposed on the flat portion 12 of the piezoelectric sensing layer 10 and/or a part of the upper surface and a part of the bottom surface of the curved portion 11. It is noteworthy that the size of the upper conductive layer 20 can be greater than, equal to, or smaller than the size of the bottom conductive layer 22, and the quantity of upper conductive layers 20 can be greater than, equal to, or smaller than the quantity of bottom conductive layers 22.

The curved portion 11 of the piezoelectric sensing layer 10 can increase the deformation of the piezoelectric sensing layer 10 to enhance the intensity of the generated physiological rhythm signal and improve the piezoelectric sensing sensitivity. On the other hand, the curved portion 11 can increase the elongation of the piezoelectric sensing layer 10 to improve the stability of sensing the physiological rhythm signal. The cover layer 50 is disposed on the upper conductive layer 20 and covered onto the information transmission controller 30 without hindering the deformation of the curved portion 11 of the piezoelectric sensing layer 10.

The bioinformatics sensing apparatus of the present invention further comprises a power supply unit 60 such as a primary battery, a secondary battery or a wireless power supply module for supplying electric power to the information transmission controller 30.

The remaining elements of this preferred embodiment such as the information transmission controller 30, the cover layer 50, the electromagnetic shielding layer and the power supply unit 60 as shown in FIG. 2 are identical to those of the previous preferred embodiment as shown in FIG. 1, so that they will not be described again.

The integrated bioinformatics sensing apparatus of the present invention can be attached onto the body surface by a conductive adhesive material such as a conductive adhesive or a double-sided conductive adhesive to improve the stability of the adhesion and the comfortability of the body surface. In the meantime, the conductivity of the conductive adhesive or double-sided conductive adhesive allows the electrical signal through the body surface to be sensed, or the integrated bioinformatics sensing apparatus of the present invention is adhered onto a patch having a relatively large area, so that users can attach the exposed patch onto the body surface directly. In the meantime, the present invention can be peeled off or removed easily to improve the convenience of use.

In summation of the description above, the present invention integrates the sensing functions of both piezoelectricity and an electrode and features a simple structure. The present invention can sense physiological rhythm and physiological electrical signals simultaneously. Particularly, the sensing apparatus can be attached onto the body surface conveniently and directly or by a conductive adhesive or set on a patch, clothes, pants, diapers, and lingerie to improve the convenience of use. Further, the invention can measure a patient's impedance pneumography or conduct a functional electrical stimulation to facilitate medical professionals to monitor and manage remote physiological information.

What is claimed is:

1. An integrated bioinformatics sensing apparatus adapted to be installed on a body surface of a living organism for sensing bioinformatics of the living organism, comprising:
at least one piezoelectric sensing layer, having at least one upper surface and at least one bottom surface, sensing a physiological rhythm of the living organism to generate a corresponding physiological rhythm signal;
at least one upper conductive layer, made of an electrically conductive material, and disposed on the upper surface of the piezoelectric sensing layer;
at least one bottom conductive layer, made of an electrically conductive material, and disposed on the bottom surface of the piezoelectric sensing layer, wherein the piezoelectric sensing layer is sandwiched between the bottom conductive layer and the upper conductive layer, and wherein the bottom conductive layer and the upper conductive layer are provided for sensing a physiological electrical signal coming from the body surface of the living organism to generate and output a physiological sensing electrical signal;
an information transmission controller, installed on the upper conductive layer, and electrically coupled to the upper conductive layer and the bottom conductive layer, with the information transmission controller receiving and processing the physiological rhythm signal and the physiological sensing electrical signal, and generating and storing sensed bioinformatics provided for loading, with the sensed bioinformatics transmitted to an external processing device via a wireless or cable transmission to display the sensed bioinformatics; and
a power supply unit supplying electric power to the information transmission controller.

2. The integrated bioinformatics sensing apparatus of claim 1, wherein the sensing apparatus is adapted to be attached to, coated on, or contacted with the body surface of the living organism, and wherein the upper conductive layer and the bottom conductive layer are attached or coated onto a part or the whole of the upper surface and the bottom surface of the piezoelectric sensing layer.

3. The integrated bioinformatics sensing apparatus of claim 1, wherein the at least one piezoelectric sensing layer senses the deformation corresponding to the physiological rhythm including at least a breathing rhythm, a heartbeat pulse, a body movement, or a muscle contraction, and wherein the physiological electrical signal at least includes an electrocardiogram, an electroencephalogram, an electromyogram, an electroneurogram, an electroretinogram, an electrogastrography, an electroneuromyography, an electrocorticogram, an electrooculography or an electronysagmography.

4. The integrated bioinformatics sensing apparatus of claim 1, wherein the piezoelectric sensing layer is a flat or curved film, sheet, wire or cable made of a material selected from the group consisting of electromechanical film, polyamide, $PbTiO_3$, quartz, $SiO_2$, $LiNbO_3$, $LiTaO_3$, $BaTiO_3$, $Pb(Zr,Ti)O_3$, GaAs, AlN, ZnO, $BiFeO_3$, polyvinylidene fluoride, polyethylene terephthalate, polyethylene, polypropylene, polyvinyl chloride, PVC, polystyrene, polytetrafluoroethene, polymethyl methacrylate, and polydimethyl siloxane.

5. The integrated bioinformatics sensing apparatus of claim 1, further comprising a cover layer, disposed on the upper conductive layer, and made of an electrically insulating material selected from the group consisting of polyamide, acrylic, acrylonitrile-butadiene-styrene, phenolic resin, epoxy, polyester, silicone, polyurethane (PU), latex, rubber, glass, food grade silicone, polyethylene terephthalate, polyethylene, polyproylene, polyvinyl chloride, polystyrene, polyvinylidene fluoride, polytetrafluoroethene, polymethyl methacrylate, and polydimethyl siloxane.

6. The integrated bioinformatics sensing apparatus of claim 5, further comprising an electromagnetic shielding layer made of a conductive electromagnetic shielding material, and disposed between the upper conductive layer and the cover layer, or disposed on the cover layer, or disposed on the bottom conductive layer, and providing an electromagnetic shielding function, with the electromagnetic shielding material including a metal, conductive plastic or conductive ceramic material.

7. An integrated bioinformatics sensing apparatus adapted to be installed on a body surface of a living organism for sensing bioinformatics of the living organism, comprising:
at least one piezoelectric sensing layer, having at least one upper surface and at least one bottom surface, sensing a physiological rhythm of the living organism to generate a corresponding physiological rhythm signal;
at least one upper conductive layer, made of an electrically conductive material, and disposed on the upper surface of the piezoelectric sensing layer; and at least one bottom conductive layer, made of an electrically conductive material, and disposed on the bottom surface of the piezoelectric sensing layer, wherein the piezoelectric sensing layer is sandwiched between the bottom conductive layer and the upper conductive layer, and wherein the bottom conductive layer and the upper conductive layer are provided for sensing a physiological electrical signal coming from the body surface of the living organism to generate and output a physiological sensing electrical signal, wherein the piezoelectric sensing layer has at least one curved portion and at least one flat portion, wherein the upper conductive layer is attached to, coated on, contacted with, or set on the piezoelectric sensing layer, and the bottom conductive layer is attached to, coated on, contacted with, or set on the piezoelectric sensing layer.

8. The integrated bioinformatics sensing apparatus of claim 7, wherein the physiological rhythm includes at least a breathing rhythm, a heartbeat pulse, a body movement, or a muscle contraction, and wherein the physiological electrical signal at least includes an electrocardiogram, an electroencephalogram, an electromyogram, an electroneurogram, an electroretinogram, an electrogastrography, an electroneuromyography, an electrocorticogram, an electrooculography or an electronysagmography.

9. The integrated bioinformatics sensing apparatus of claim 7, wherein the piezoelectric sensing layer is made of a material selected from the group consisting of electromechanical film, polyamide, $PbTiO_3$, quartz, $SiO_2$, $LiNbO_3$, $LiTaO_3$, $BaTiO_3$, $Pb(Zr,Ti)O_3$, GaAs, AlN, ZnO, $BiFeO_3$, polyvinylidene fluoride, polyethylene terephthalate, polyethylene, polypropylene, polyvinyl chloride, PVC, polystyrene, polytetrafluoroethene, polymethyl methacrylate, and polydimethyl siloxane.

10. The integrated bioinformatics sensing apparatus of claim 8, further comprising a cover layer and an electromagnetic shielding layer, wherein the cover layer is disposed on at least one upper conductive layer, and is made of an electrically insulating material selected from the group consisting of polyamide, acrylic, acrylonitrile-butadiene-styrene, phenolic resin, epoxy, polyester, silicone, polyurethane (PU), latex, rubber, glass, food grade silicone, polyethylene terephthalate, polyethylene, polyproylene, polyvinyl chloride, polystyrene, polyvinylidene fluoride, polytetrafluoroethene, polymethyl methacrylate, and polydimethyl siloxane; with the electromagnetic shielding layer made of a conductive electromagnetic shielding material, and disposed between at least one upper conductive layer and the cover layer, or disposed on the cover layer, or disposed on the bottom conductive layer, and providing an electromagnetic shielding function, and with the electromagnetic shielding material including a metal, conductive plastic or conductive ceramic material.

11. The integrated bioinformatics sensing apparatus of claim 7, wherein the upper conductive layer is attached to, coated on, contacted with, or set on the at least one curved portion of the piezoelectric sensing layer or a part or the whole of the upper surface of the at least one flat portion, and wherein the bottom conductive layer is attached to, coated on, contacted with, or set on the at least one curved portion of the piezoelectric sensing layer, or a part or the whole of the bottom surface of the at least one flat portion.

12. The integrated bioinformatics sensing apparatus of claim 7, wherein the upper conductive layer is attached to, coated on, contacted with, or set on a part or the whole of the upper surface of the at least one flat portion, and wherein the bottom conductive layer is attached to, coated on, contacted with, or set on a part or the whole of the bottom surface of the at least one flat portion.

* * * * *